(12) United States Patent
Kim et al.

(10) Patent No.: US 9,050,301 B2
(45) Date of Patent: Jun. 9, 2015

(54) PHARMACEUTICAL COMPOSITION FOR TREATMENT OF CORNEAL ENDOTHELIAL WOUNDS CONTAINING ANGIOGENIN

(71) Applicants: Chung-Ang University Industry-Academy Cooperation Foundation, Seoul (KR); Chungbuk National University Industry-Academic Cooperation Foundation, Cheongju-si, Chungcheongbuk-do (KR); Industry Academic Cooperation Foundation, Hallym University, Chuncheon-si, Gangwon-do (KR)

(72) Inventors: Jae Chan Kim, Seoul (KR); Kyoung Woo Kim, Seoul (KR); Yeoun Sook Chun, Seoul (KR); Soo Hyun Park, Seoul (KR); Sung Wook Wee, Seoul (KR); Soo Ik Chang, Daejeon (KR); Kyong Mi Min, Cheongju-si (KR); Kyu Wan Kim, Cheongju-si (KR); Young Joo Shin, Seoul (KR)

(73) Assignees: CHUNG-ANG UNIVERSITY INDUSTRY-ACADEMY COOPERATION FOUNDATION, Seoul (KR); CHUNGBUK NATIONAL UNIVERSITY INDUSTRY-ACADEMIC COOPERATION FOUNDATION, Chungcheongbuk-Do (KR); INDUSTRY ACADEMIC COOPERATION FOUNDATION, HALLYM UNIVERSITY, Gangwon-Do (KR)

( * ) Notice: Subject to any disclaimer, the term of this patent is extended or adjusted under 35 U.S.C. 154(b) by 0 days.

(21) Appl. No.: 14/493,375

(22) Filed: Sep. 23, 2014

(65) Prior Publication Data

US 2015/0086527 A1    Mar. 26, 2015

(30) Foreign Application Priority Data

Sep. 23, 2013   (KR) .................. 10-2013-0112888

(51) Int. Cl.
    A61K 38/18      (2006.01)
    A61K 38/46      (2006.01)
    C07K 14/515     (2006.01)

(52) U.S. Cl.
    CPC ........... *A61K 38/1891* (2013.01); *A61K 38/465* (2013.01); *C12Y 301/27* (2013.01); *C07K 14/515* (2013.01)

(58) Field of Classification Search
    IPC .......................... A61K 38/1891; C07K 14/515
    See application file for complete search history.

(56) References Cited

U.S. PATENT DOCUMENTS

2002/0055117 A1* 5/2002 Fett et al. .................... 435/6

FOREIGN PATENT DOCUMENTS

KR       2013-0037477 A      4/2013

OTHER PUBLICATIONS

Kim et al., "The inhibitory effects of recombinant plasminogen kringle 1-3 on the neovascularization of rabbit cornea induced by angiogenin, bFGF, and VEGF," Experimental and Molecular Medicine 31(4):203-209, 1999.*

*Primary Examiner* — Rosanne Kosson
(74) *Attorney, Agent, or Firm* — Revolution IP, PLLC

(57) ABSTRACT

Provided is a pharmaceutical composition for treating corneal endothelium wounds, the composition including angiogenin as an effective ingredient. The present invention relates to a new topical therapeutic use of angiogenin for treatment of corneal endothelium wounds, wherein the angiogenin that is generally known to be involved in angiogenesis activates a PI3K/Akt/eNOS pathway thereof in ocular corneal endothelium to increase migration and proliferation of corneal endothelial cells that are not capable of self-proliferation and to promote prevention and treatment of corneal endothelial cell wounds.

5 Claims, 10 Drawing Sheets

(HCEn, Human corneal endothelial cell)

PHARMACEUTICAL COMPOSITION FOR TREATMENT OF CORNEAL ENDOTHELIAL WOUNDS CONTAINING ANGIOGENIN

CROSS-REFERENCE TO RELATED PATENT APPLICATION

This application claims the benefit of Korean Patent Application No. 10-2013-0112888, filed on Sep. 23, 2013, in the Korean Intellectual Property Office, the disclosure of which is incorporated herein in its entirety by reference.

BACKGROUND OF THE INVENTION

1. Field of the Invention

The present disclosure relates to novel use of angiogenin for treatment of corneal endothelial wounds.

2. Description of the Related Art

Human corneal endothelial cells organize a physiologically most important single cell layer that maintains corneal transparency by controlling moisture movement based on dynamic equilibrium between leaky barrier functions and active pumping actions. However, the corneal endothelial cells that are damaged in vivo are extremely limited for regeneration. Thus, when the endothelial cells are damaged by several diseases such as Fuchs' dystrophy, wounds, pseudophakic bullous keratopathy, or the like, the endothelial cells may cause corneal edema and opacity and accordingly, may result in severe loss of sight.

These human corneal endothelial cells are quiescent in the $G_1$ phase of the cell cycle throughout their lifetime, and at the same time, may be able to heal damaged areas by increased cell migration and cell size, whereas most cells are associated with cell proliferation and migration in the process of wound healing due to increased expression of a number of regulators such as a p53 gene that inhibits the cell cycle progression. The human corneal endothelial cells do not proliferate by cell division, but according to the recently published reports, it is reported that there are sites for the centripetal proliferation and migration of endothelial cells from the corneal endothelial periphery present around the extreme periphery of corneal endothelium (He Z, & Campolmi N, & Gain P, & Ha Thi BM, & Dumollard J M, & Duband S, & Peoc'h M, & Piselli S, & Garraud O, & Thuret G. Revisited microanatomy of the corneal endothelial periphery: new evidence for continuous centripetal migration of endothelial cells in humans. Stem Cells. 2012; 30:2523-2534).

Angiogenin is a 14.4-kDa single chain protein of 123 amino acids, and is one of secreted proteins capable of inducing angiogenesis along with a vascular endothelial growth factor (VEFG). In regard to mechanisms for proliferation of the endothelial cells upon angiogenesis, it is known that the PI3k-Akt-endothelial nitric oxide synthase (eNOS) pathway and the extracellular signal-regulated kinase (Erk) pathway become activated and nitric oxide (NO) induced by the eNOS may prevent apoptosis of the vascular endothelial cells and enhance migration thereof.

It is found that the flow of aqueous humor in the eyes has a similar shearing force with that of the blood flow which is regarded as a stimulatory factor for proliferation of the vascular endothelial cells and is directly adjacent to the corneal endothelial cells, and that the angiogenin-associated pathway in the vascular endothelial cells is significantly similar to the survival pathway of the human corneal endothelial cells. In this regard, angiogenin is configured to be used for treatment of corneal endothelium wounds.

Angiogenin described herein is a material that is not much researched in the field of ophthalmology yet. However, according to Korean Patent Application No. 10-2013-0037477, angiogenin is disclosed as a composition for preventing or treating inflammatory disease, and the disclosed invention describes that ocular disease is associated with anti-immune therapy for preventing or treating decreased visual acuity, which is caused by angiogenesis and opacification of the corneal stroma due to chronic ocular inflammation and immune response by cataract, glaucoma, eye injury or the like. Meanwhile, the disclosure of the present invention is configured to activate the PI3k-Akt-eNOS pathway of angiogenin in the corneal endothelial cells that are not capable of self-proliferation, wherein angiogenin is identified to be effective in promoting healing of the human corneal endothelium wounds.

SUMMARY OF THE INVENTION

Provided is a pharmaceutical composition including angiogenin as an effective ingredient for treating corneal endothelium wounds.

Additional aspects will be set forth in part in the description which follows and, in part, will be apparent from the description, or may be learned by practice of the presented exemplary embodiments.

Damages to the corneal endothelial cells are important issues that are directly related to visual prognosis, but these corneal endothelial cells are not capable of self-proliferation unlike other cells, and accordingly, there are many difficulties in the treatment of wounds. In order to solve such problems, the present invention discloses a wound therapeutic use of angiogenin by activating the PI3k/Akt/eNOS pathway thereof to enhance migration and proliferation of the corneal endothelial cells.

The angiogenin is capable of activating its PI3K/Akt/eNOS pathway.

The content of the angiogenin is about 0.01 parts to about 10 parts by weight based on 100 parts by weight of the pharmaceutical composition.

The formulation of the pharmaceutical composition is any one selected from the group consisting of instillations, injections, granules, tablets, pills, capsules, gels, syrups, suspensions, emulsions, drops, and solutions.

The pharmaceutical composition can further include at least one additive selected from the group consisting of carriers, excipients, disintegrants, sweetners, coating agents, swelling agents, glydents, flavouring agents, antioxidants, buffers, bacteriostatics, diluents, dispersants, surfactants, binders, and lubricants.

Therefore, the present invention relates to novel topical therapeutic use of angiogenin for treatment of corneal endothelium wounds, wherein the angiogenin known to be involved in angiogenesis in the art activates its PI3K/Akt/eNOS pathway in ocular corneal endothelium to enhance migration and proliferation of the corneal endothelial cells that are not capable of self-proliferation and to promote prevention and treatment of the corneal endothelial cell wounds.

BRIEF DESCRIPTION OF THE DRAWINGS

These and/or other aspects will become apparent and more readily appreciated from the following description of the exemplary embodiments, taken in conjunction with the accompanying drawings in which:

FIG. 2 shows results of corneal transparency measured in a control group, a Y-27632 treating group, and an angiogenin treating group after making damages to the rabbit corneal endothelium, in which

FIG. 5 are images obtained by staining the rabbit corneal endothelial cells immediately before and after making damages to the rabbit trans-corneal endothelial cells, in which

FIG. 10 shows results of a case treated with angiogenin only and a case treated with LY294002 and angiogenin, obtained after 72 hours of making damages to the rabbit corneal endothelium angiogenin, in which

FIG. 11 shows results obtained by treating corneal endothelial cells with LY294002 and angiogenin according to the hours after making damages to human corneal endothelial cells, in which FIG. 12 shows results for the analysis of expression of a target protein at a latter half of the angiogenin pathway, in which

DETAILED DESCRIPTION OF THE INVENTION

Figure 1:
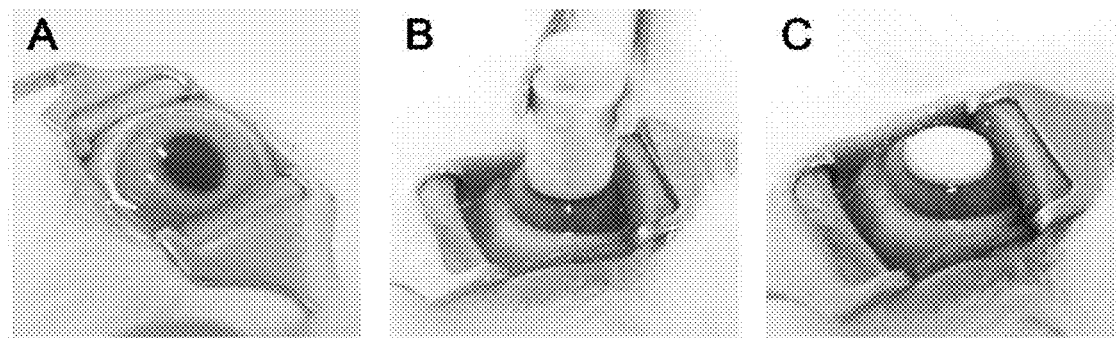
FIG. 1 is a view describing a process of inducing damages to central corneal endothelium in rabbits by performing transcorneal freezing.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list.

The present invention discloses that angiogenin known to be involved in angiogenesis in the related art is also effective in cell migration and proliferation in corneal endothelium, and accordingly, describes a use of angiogenin for treatment of corneal endothelium wounds.

Thus, an aspect of the present invention provides a pharmaceutical composition including angiogenin as an effective ingredient for treating corneal endothelium wounds.

The angiogenin may activate PI3K/Akt/eNOS pathway.

Figure 10A:
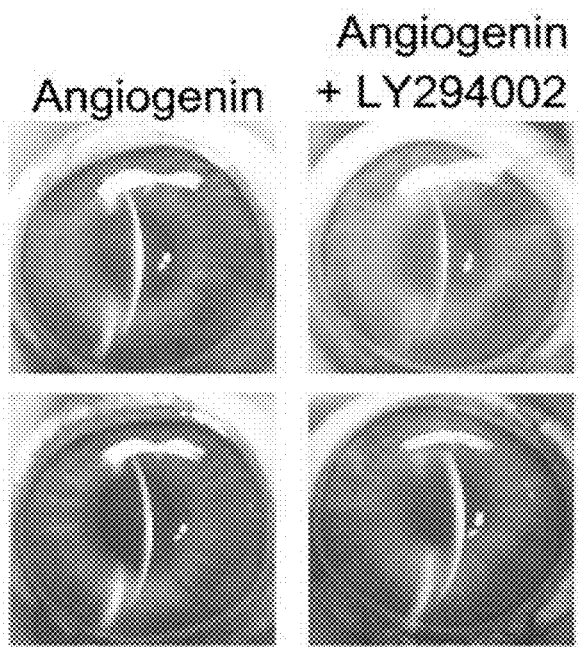
FIG. 10A shows slit lamp microscope images of corneal transparency of each experimental group and FIG. 10B is a graph statistically analyzing corneal transparency of each experimental group.
Figure 10B:
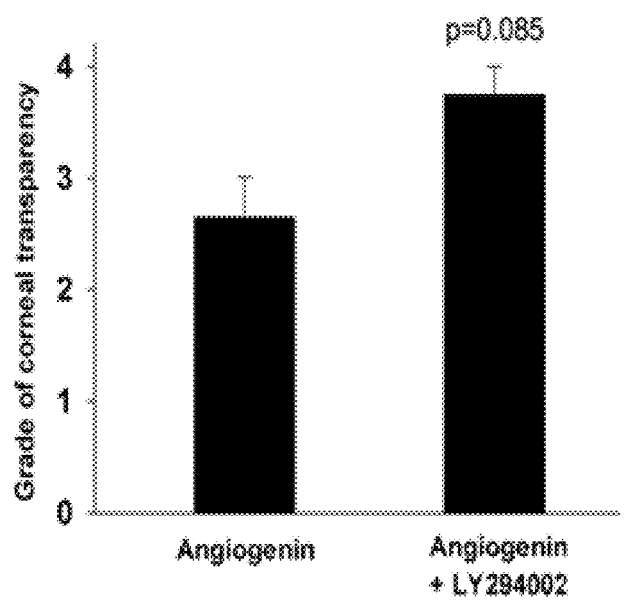

Referring to FIGS. 10A and 10B, the progression of corneal opacities in a case of administrating LY294002 as an inhibitor of the PI3K/Akt pathway and angiogenin together, and a case of administrating angiogenin only. In the case of administrating LY294002 and angiogenin together, it is confirmed that the corneal opacity has progressed as compared with the case of administrating angiogenin only. That is, there is provided a pharmaceutical composition including angiogenin for treating corneal endothelium wounds, wherein the angiogenin activates the PI3K/Akt/eNOS pathway, increases proliferation of corneal endothelial cells, and suppresses the cornea opacities.

The angiogenin may be contained in an amount of about 0.01 parts to about 10 parts by weight based on 100 parts by weight of the pharmaceutical composition.

In some embodiments, the pharmaceutical composition including angiogenin as an effective ingredient for treating corneal endothelium wounds may be used in any one of formulations selected from the group consisting of instillations, injections, granules, discutients, tablets, pills, capsules, suppositories, gels, suspensions, emulsions, droppers, and solutions.

In some other embodiments, the pharmaceutical composition including angiogenin as an effective ingredient for treating corneal endothelium wounds may further include at least one suitable additive, which is generally used in preparation of a pharmaceutical composition, selected from the group consisting of carriers, excipients, disintegrants, sweetners, coating agents, swelling agents, glydents, flavouring agents, antioxidants, buffers, bacteristats, diluents, dispersants, surfactants, binders, and lubricants.

Detailed examples of carriers, excipients, and diluents include lactose, dextrose, sucrose, sorbitol, mannitol, xylitol, erythritol, maltitol, starch, acacia gum, alginate, gelatin, calcium phosphate, calcium silicate, cellolose, methyl cellulose, microcrystalline cellulose, polyvinyl pyrrolidone, water, methyl hydroxybenzoate, propyl hydroxybenzoate, talc, magnesium stearate, and mineral oil. In consideration of solid formulations for oral administration, the composition may be used in the formulation of tablets, pills, discutients, granules, or capsules. These solid formulations may be prepared by mixing the composition with at least one excipient, such as starch, calcium carbonate, sucrose or lactose, or gelatin. In addition to these simple excipients, lubricants such as magnesium stearate and talc may be used in preparation of the solid formulation. In consideration of liquid formulations for oral administration, the composition may be used in the formulation of suspensions, solutions, emulsions, or syrups. In addition to simple diluents such as water, liquid and liquid paraffin that are commonly used, various types of excipients such as wetting agents, sweetening agents, flavoring agents, and preservatives may be included in the composition. Meanwhile, formulations for parenteral administration may include sterilized aqueous solutions, non-aqueous solvents, suspensions, emulsions, freeze-drying agents, suppositories, or the like. Examples of the non-aqueous solvents and suspensions include propylene glycol, polyethylene glycol, vegetable oil such as olive oil, or injectable ester such as ethylolate. Examples of suppositories include witepsol, macrogol, tween 61, cacao butter, laurin butter, or glycerinated genetine.

In some other embodiments, the pharmaceutical composition may be administrated to a subject in a conventional manner, e.g., intravenous, intraarterial, intraperitoneal, intramuscular, intrasternal, percutaneous, endonasal, inhaled, topical, rectal, oral, intraocular, o intradermal pathway.

A desirable dosage of the angiogenin may vary according to a subject's condition, weight, type and extent of the disease, drug form, route of administration, and medication time by one of ordinary skill in the art. A daily dosage of the angiogenin may be, but is not limited, in a range of about 0.01 mg/kg to about 200 mg/kg, specifically, about 0.1 mg/kg to about 200 mg/kg, and more specifically, about 0.1 mg/kg to about 100 mg/kg. The angiogenin may be administrated once a day or administrated several times, but the administration is not limited thereto.

As used herein, the term 'subject' may refer to a mammal including a human, but is not limited thereto.

Hereinafter, the present invention will be described in detail by explaining preferred embodiments of the invention with reference to the attached drawings. Like reference numerals in the drawings denote like elements, and thus their description will not be repeated.

Reference Example below is to provide a reference commonly applied to each of Examples according to the present invention.

REFERENCE EXAMPLE

Statistical Analysis

Corneal transparency grades/gradients, thickness of central cornea, observation of corneal endothelium wounded areas by alizarin red S-staining, and in vitro wounded areas were examined and compared between groups according to a Mann-Whitney U test using a statistical analysis software SPSS (version 19.0, SPSS Inc., Chicago, USA), wherein a predetermined p less than 0.05 ($p<0.05$) was determined to be statistically significant and measurements were represented as mean±standard error (SE).

Example 1

Analysis of Wound Healing Effects on In Vivo Corneal Endothelium of Angiogenin

1. Corneal Endothelium Damages in Eyes of Rabbits

All experiments were carried out according to the Association for Research in Vision and Ophthalmology (ARVO) guidelines for animal experiments.

30 eyeballs of 15 healthy white New Zealand rabbits weighing about 2.0 kg to about 3.0 kg without external opacification were anesthetized by intramuscular injection with 12.5 mg/kg of tiletamine/zolazepam (Zoletil®, VirbacLab, France) and 12.5 mg/kg of zylazine (Rompun®, BayerKorea, Korea). Afterwards, 0.5% povidone-iodine was used for disinfection of the whole range of experimental sight. The damage to the rabbit corneal endothelium was induced as shown in FIG. 1. Referring to FIG. 1, an 8 mm-diameter stainless steel rod as a probe was immersed in liquid nitrogen for 3 minutes, removed therefrom once the temperature of the liquid nitrogen reached $-196°$ C., and brought into contact to the central cornea for 15 seconds. Then, each of the eyeballs was washed with 10 cc of 0.9% saline solution. In order to prevent the occurrence of corneal infection, the rabbit corneas were given instillation of Levofloxacin (Cravit®, Santen, Japan) three times a day for 3 days after the damage was induced.

3 groups consisting of 10 eyeballs given instillation of angiogenin (200 µg/mL), 7 eyeballs given Y-27632 (10 mM) inhibitor of Rho-associated coiled-coil kinase (ROCK) pathway, and 7 eyeballs as a control group given phosphate-buffered solution (PBS) were each subjected to 50 µl of instillation at a time, and more particularly, 6 times a day for the first 2 days, and then, 4 times a day for the following 2 days, starting immediately after inducing freeze-damages to the trans-corneal endothelium. That is, the instillation was performed 20 times in total for 4 days.

2. Analysis of Angiogenin Effects on Corneal Transparency Improvement

After inducing freeze-damages to trans-corneal of all the eyeballs from a group given instillation of angiogenin, a group given installation of Y-27632, and a control group, the extent of corneal transparency of the groups were observed at every 48 hours ($2^{nd}$ day), 72 hours ($3^{rd}$ day), 144 hours ($6^{th}$ day), and 192 hours ($8^{th}$ day) according to the method of Table 1 and were objectively graded by using a slit lamp microscope. Then, the groups were subjected to the evaluation of corneal opacity and corneal edema by using a digital camera (VLUUNV100HD, Samsung, Suwon, Korea) to obtain images taken in a diagonal direction.

Figure 2A:
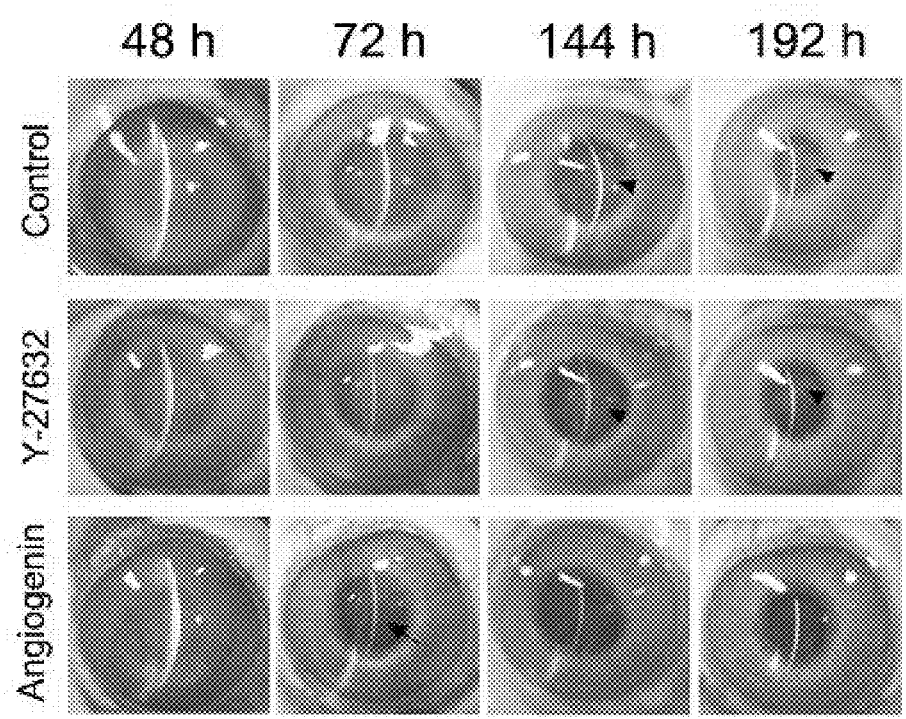
FIG. 2A shows slit-lamp microscope images of corneal transparency according to the observation times.
Figure 2B:
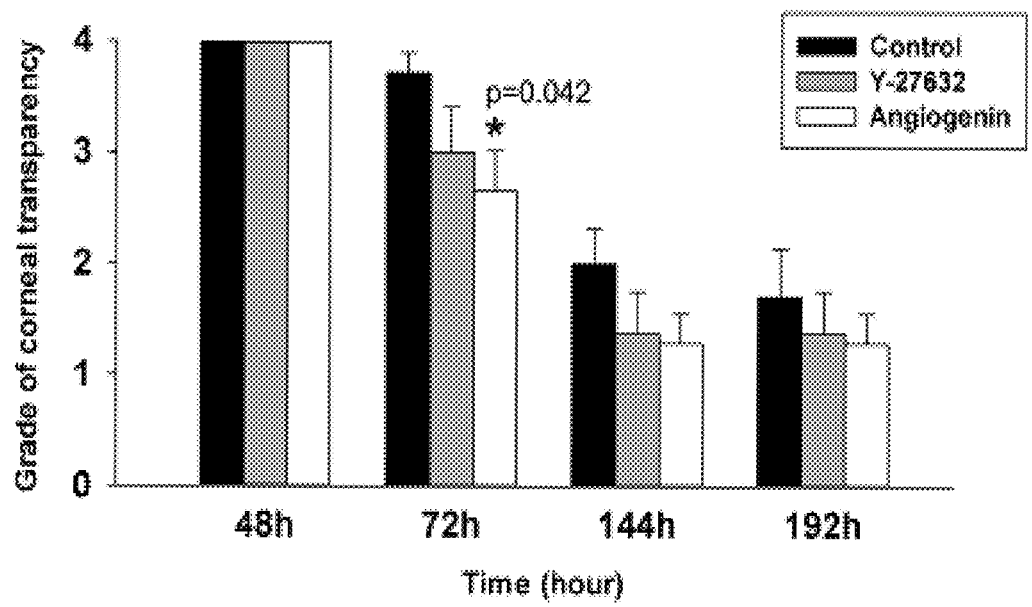
FIG. 2B is a graph statistically analyzing corneal transparency after 72 hours of drug treatment.
Figure 3:
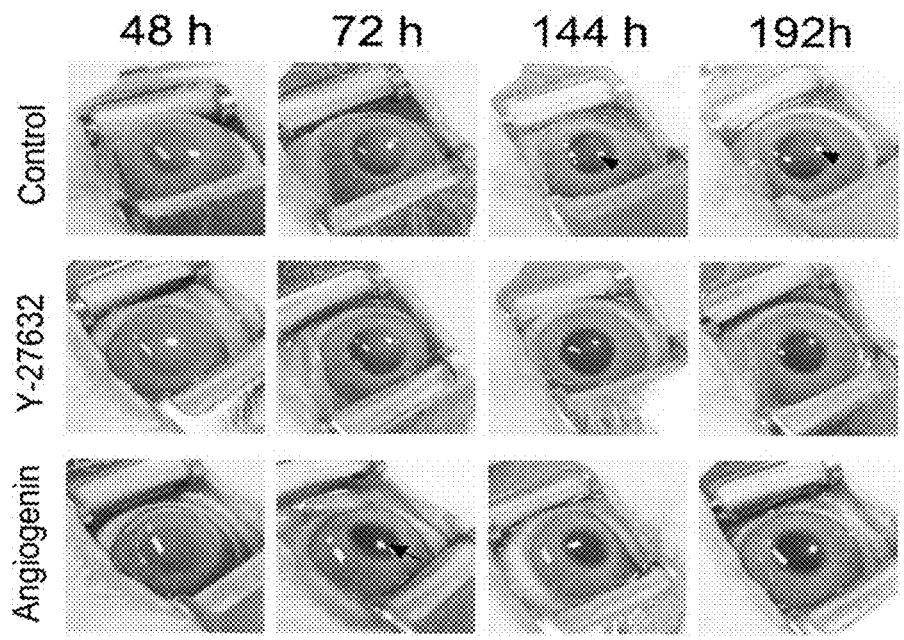
FIG. 3 shows digital camera images of corneal transparency in an experimental group and a control group according to the observation times, each of which is treated by drug after making damages to the rabbit corneal endothelium.

As a result, referring to FIG. 2A and Table 2, the corneal transparency observed by a slit-lamp microscope was the most transparent in the group given angiogenin instillation at every observation time of 72 hours (3 days), 144 hours (6 days), and 192 hours (8 days). Referring to FIG. 2B, the group given angiogenin instillation showed significant difference from the control group at the observation time of 72 hours ($p=0.042$). Also, in order to evaluate the presence of the corneal opacity and edema, it was confirmed according to the cornea images obtained by the digital camera in a diagonal direction showed that, as shown in FIG. 3 and Table 2, the group given angiogenin instillation had the highest fraction in terms of not including the corneal opacity and edema at the observation time of 72 hours ($3^{rd}$ day), 144 hours ($6^{th}$ day), and 192 hours ($8^{th}$ day).

3. Analysis of Angiogenin Effects on Central Corneal Thickness and Corneal Opacity Improvement After inducing freeze-damages to trans-corneal of all the eyeballs from the group given instillation of angiogenin, the group given instillation of Y-27632, and the control group, the central corneal thickness was measured 3 times by using an ultrasonic corneal pachymeter (POCKET-II, Quantel medical, Clemont-Ferrand, France) at every 48 hours ($2^{nd}$ day), 72 hours ($3^{rd}$ day), 144 hours ($6^{th}$ day), and 192 hours ($8^{th}$ day), thereby calculating a mean value thereof. Here, the maximum measurable value of the ultrasonic corneal pachymeter was referred to 1,000 µm so the maximum corneal thickness was also considered as 1,000 µm.

Figure 4:
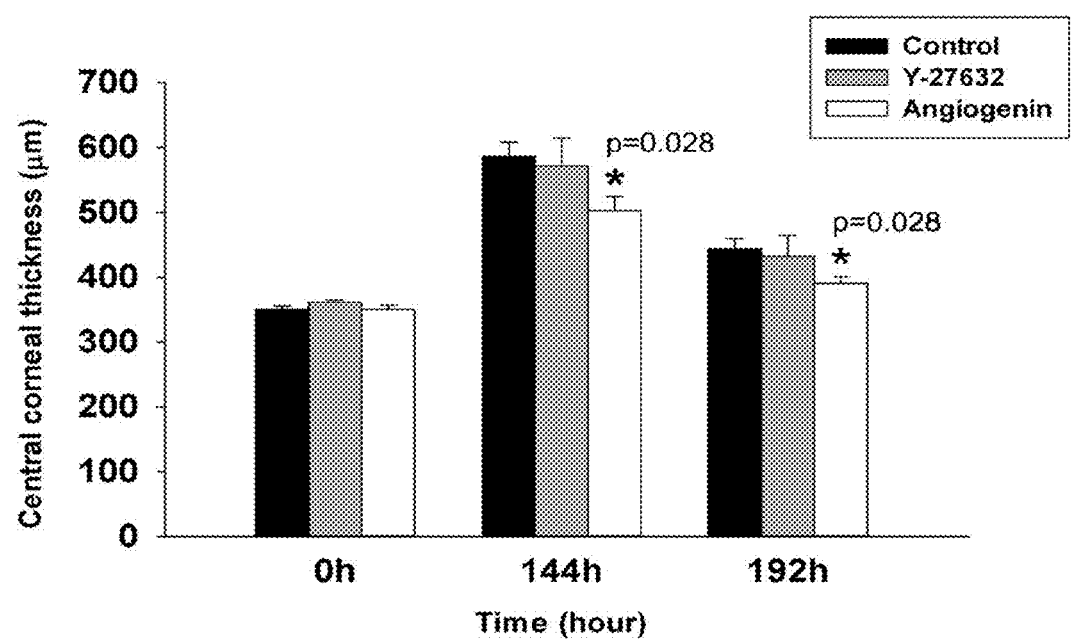
FIG. 4 is a graph showing a mean value of central corneal thickness obtained by measuring three times using an ultrasonic pachymeter a thickness of the rabbit corneal endothelium of an experimental group and a control group according to the observation times, each of which is treated by drug after making damages to the rabbit corneal endothelium.

As a result, referring to FIG. 4, the central corneal thickness was measured 144 hours (6$^{th}$ day) after inducing the endothelial damages, and it was confirmed that the group given angiogenin instillation had the smallest central corneal thickness of about 503.0±21.07 μm and about 390.3±10.55 μm measured at the observation time of 144 hours (6$^{th}$ day) and 192 hours (8$^{th}$ day), respectively. These thickness values were the smallest among the measurements of the other groups, and accordingly, the group given angiogenin instillation showed significant results from the control group. In addition, as shown in Table 3, the group given Y-27632 instillation also had small central corneal thickness at the observation time of 144 hours and 192 hours as compared with the central corneal thickness of the control group, but the results obtained therefrom were not statistically significant.

4. Analysis of Angiogenin Effects on Corneal Endothelium Wound Healing

Two eyeballs out of 30 eyeballs in total were each used as a negative control group of normal corneal endothelium and as a positive control group being subjected to alizarin red S-staining immediately after inducing freeze-damages to the trans-corneal endothelium. An overdose of KCl was administrated into the rest of the eyeballs by intramuscular injection 192 hours (8$^{th}$ day) after inducing freeze-damages to the trans-corneal, and accordingly, these eyeballs were sacrificed. Then, 3 eyeballs were removed for each of the control group, the group given angiogenin instillation, and the group given Y-27632 instillation. Then, the whole cornea was pulled off with respect to the corneal limbal boundary, immersed in 1% alizarin red S-staining solution (Lab Chem, Pittsburgh, USA) for 2 minutes, washed with 0.9% saline solution, and then, wet-mount with the endothelium facing upward. Images thereof were immediately obtained after observation by using an optical microscope, and then, the wounded area of the cornea was measured in pixels for a digital image at 40× magnification by using the Image J software (National Institutes of Health (NIH); http://rsbweb.nih.gov/ij/), and the endothelial cells around the wounded areas were observed and compared in terms of hexagonality at 200× magnification.

Figure 5A:
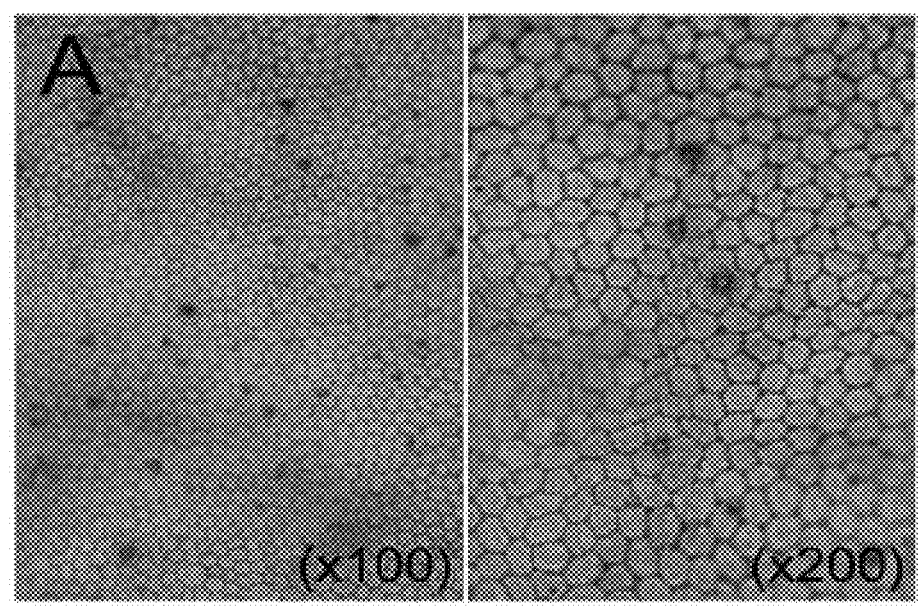
FIG. 5A is an image obtained by staining the rabbit corneal endothelial cells before making damages to the rabbit trans-corneal endothelial cells and FIG. 5B is an image obtained by staining the rabbit corneal endothelial cells after making damages to the rabbit trans-corneal endothelial cells.
Figure 5B:
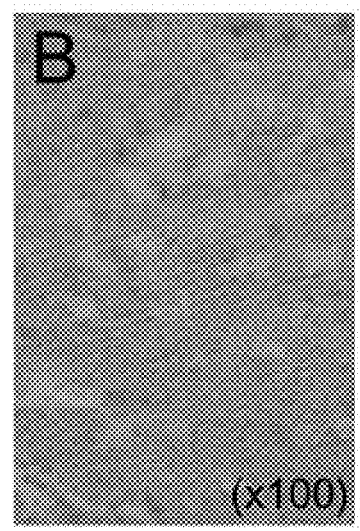

As a result, referring to FIG. 5A, it was confirmed that the negative control group with corneal endothelium staining using 1 eyeball prepared before and after inducing freeze-damages to the trans-cornea had corneal endothelial cells arranged in a hexagonal, dense structure, whereas referring to FIG. 5B, it was confirmed that the positive control group had clearly revealed the descemet's membrane without corneal endothelial cells. In this regard, it was deemed that the freeze-damages to the trans-cornea was a suitable method to induce endothelial damages.

Figure 6A:
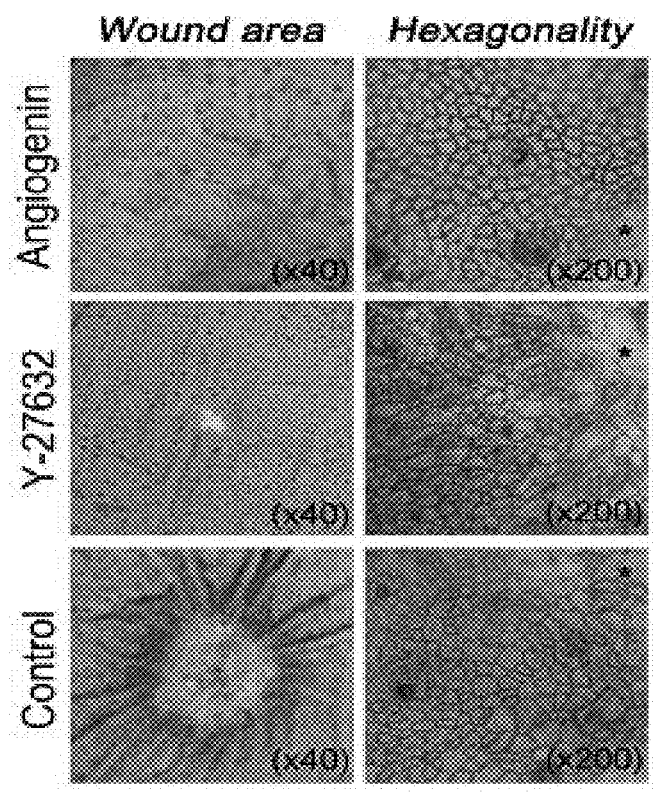
FIG. 6A shows images obtained by staining corneal endothelium wounds of an experimental group and a control group, each of which is treated by drugs, at the maximum elapsed time, 192 hours (8$^{th}$ day) after making damages to the rabbit corneal endothelium.
Figure 6B:
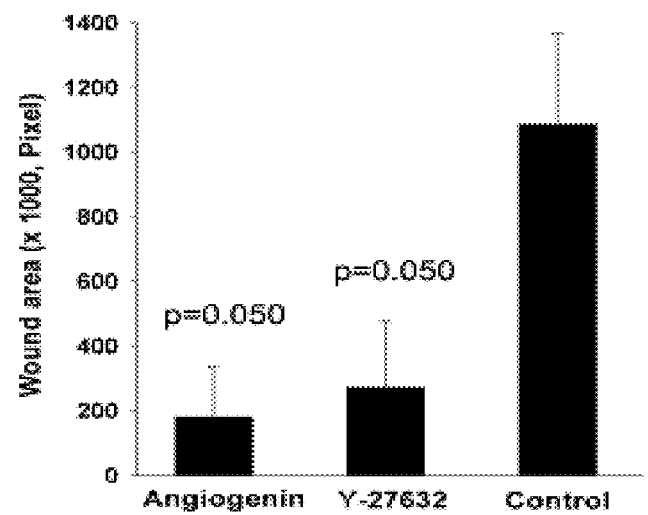
FIG. 6B is a graph statistically analyzing boundaries of wounded areas.

In addition, as shown in FIG. 6A, it was confirmed that the group given angiogenin instillation had the smallest the corneal endothelium wounded area as observed by alizarin red S-staining at the maximum observation time of 192 hours (8$^{th}$ day). Both of the groups each given angiogenin and Y-27632 instillation had smaller wounded areas than those of the control group, and as shown in FIG. 6A, the boundary values of the same groups had statistically significant difference from the control group (p=0.050). When observing the endothelial cells around the wounded area at 200× magnification, the group given angiogenin instillation usually had corneal endothelial cells in even hexagonality while the group given Y-27632 instillation and the control group had significant modification of cell morphology.

Example 2

Analysis of Angiogenin Effects on In Vitro Migration and Proliferation of Corneal Endothelial Cells 1. Culturing of Rabbit and Human Corneal Endothelial Cells A corneal endothelial tissue segment obtained from remaining corneal portions other than the central 8 mm corneal portion in cadaveric cornea donated for transplantation and a corneal endothelial tissue segment of a normal rabbit were cultured. Then, each of the corneal tissues was divided into 6 pieces and washed by shaking 6 times in a petri dish to which 7 ml of 5% penicillin/streptomycin (P/S) was added. Then, the washed tissues were each transferred to a 6-well dish such that the endothelial layer was facing down, and the tissues were semi-dried until the dishes were slightly drained. Next, the corneal endothelial cells of the rabbit cornea were cultured in a culture medium (EGM™-2BulletKit™, Lonza, Allendale, USA) containing human epidermal growth factor (hEGF), hydrocortisone, 5% fetal bovine serum (FBS), human mesenchymal stem cell growth factor (hFGF), insulin-like growth factor (IGF), ascorbic acid, gentamicin, and amphotericin-B (EGM™-2BulletKit™, Lonza, Allendale, USA), and the corneal endothelial cells of the human cornea were cultured in a culture medium (Opti-MEM®, Gibco®, New York, USA) supplemented with 8% FBS, calcium ($CaCl_2$), chondroitinsulfate, ascorbic acid, multi-vitamin solution, gentamicin, anti-*Pseudomonas aeruginosa* antibiotic, pituitary extract, epidermal growth factor (EGF), and nerve growth factor (NGF), for about 5 to 7 days.

2. In Vitro Wound Healing Experiments of Cultured Corneal Endothelial Cells

Experiments have been carried to identify angiogenin effects on migration and proliferation of the corneal endothelial cells. When the cultured rabbit corneal endothelial cells had about 80-90% confluency in three 6-well dishes, the central part of each well was scratched by a tip of a 200 μl pipette to make wounds. Then, each of the three 6-well dishes was replaced by a culture medium containing 1) 5% FBS (in the control group), 2) Y-27632 (10 μM), and 3) angiogenin (2 μg/ml). At every 0 hour, 12 hours, 24 hours, and 48 hours, digital images of the remaining wounded areas were obtained at 40× magnification of the optical microscope, and measured in pixels by using the Image J software. In addition, each of the three 6-well dishes containing the cultured corneal endothelial cells in the human was scratched in the same manner as described above to make wounds, and then, replaced by a culture medium containing 1) 5% FBS (in the control group), 2) Y-27632 (10 μM), and 3) angiogenin (5 μg/ml). At every 6 hours and 24 hours, the wounded areas were measured by using the Image J software. The ratio of initial wounded area versus recovered area was defined as wound healing index, which is calculated as shown below. Here, the initial wounded area was corrected to be equal before the calculation.

Figure 7A:
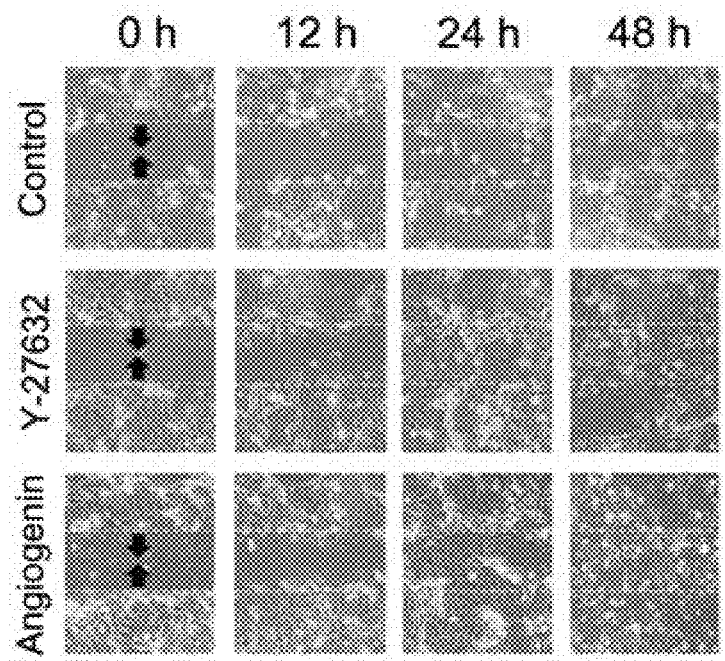
FIG. 7 shows results of an experimental group and a control group, each of which is treated by drugs, obtained by culturing a tissue fragment of normal rabbit corneal endothelium, in which 7A shows optical microscope images taken at a magnification of 40× according to each elapsed time
FIG. 7B is a graph showing wound healing index according to the hours.
Figure 7B:
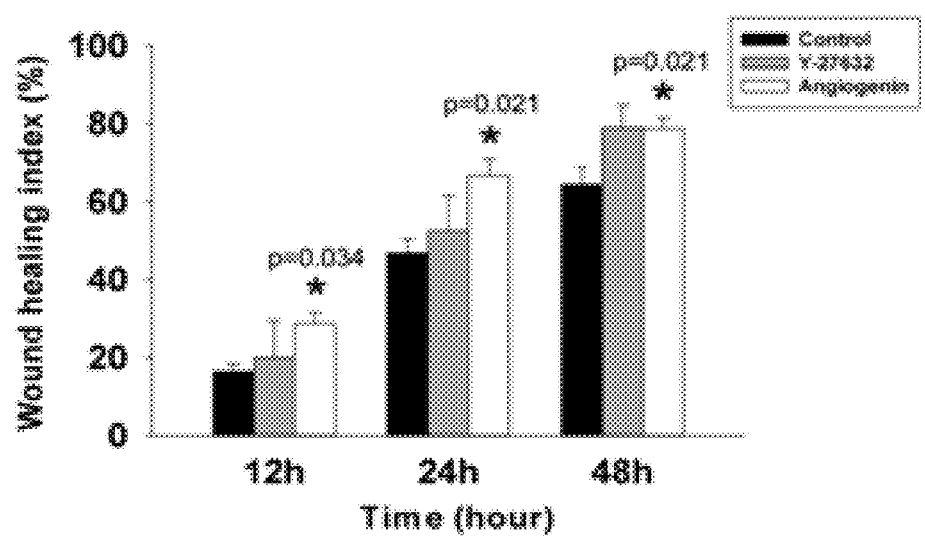
Figure 8A:
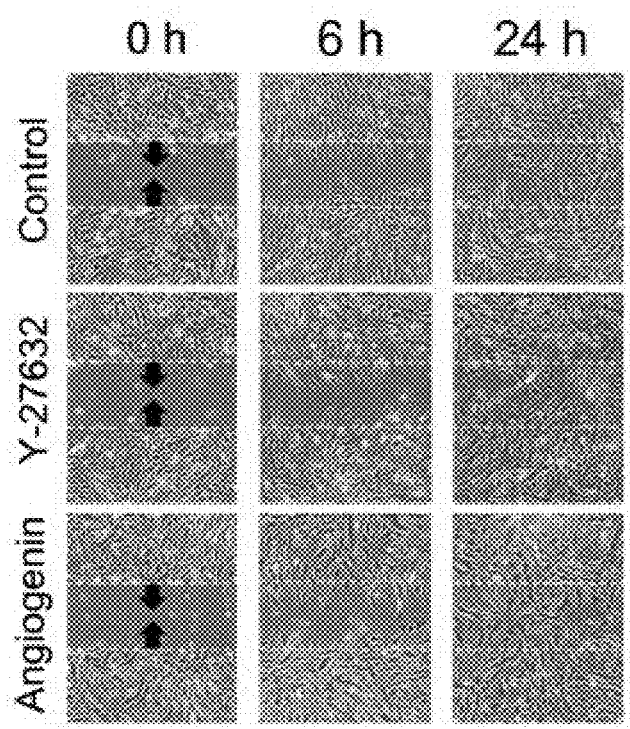
FIG. 8 shows results of an experimental group and a control group, each of which is treated by drugs, obtained by culturing human corneal endothelial cells, in which 8A shows optical microscope images taken at a magnification of 40× according to each elapsed time
FIG. 8B is a graph showing wound healing index according to the hours.
Figure 8B:
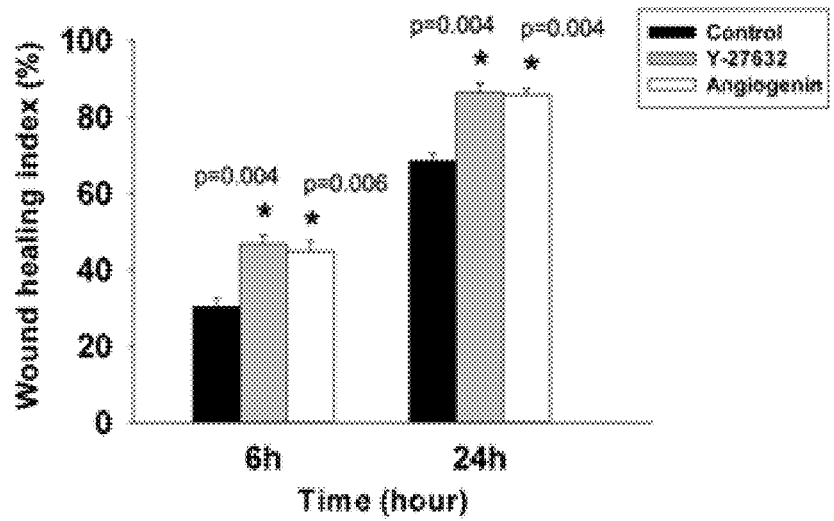

Wound healing index(%)=(Initial wounded area−Remaining wounded area)/Initial wounded area As a result, the rabbit corneal endothelial cells in the group given angiogenin instillation had the wound healing indexes (%) of, as shown in FIGS. 7A and 7B, 28.7±2.9%, 66.7±4.3%, and 78.7±2.9% at every observation hours of 12, 24, and 48 hours, respectively. These wound healing indexes were significantly higher than the wound healing indexes of 16.5±1.9%, 46.9±3.5%, and 64.4±4.6% in the control group. The group given Y-27632 instillation and the control group did not show significant difference therebetween in terms of the wound healing index. In addition, the human corneal endothelial cells had high wound healing index, as shown in FIGS. 8A and 8B, in both the groups each given angiogenin and Y-27632 instillation at every 6 and 24 hours, as compared with the wound healing index of the control group. Meanwhile, the cultured endothelial cells in the human and the rabbit did not show significant difference in the group given angiogenin instillation and the group given Y-27632 instillation.

3. Identification of Appropriate Concentration for In Vitro Wound Healing of Cultured Human Corneal Endothelial Cells Experiments have been carried to identify optimal concentration of angiogenin to improve in vitro migration and proliferation improvement of the cultured human corneal endothelial cells. When the cultured human corneal endothelial cells had about 80-90% confluency in four 6-well dishes, the central part of each well was scratched by a tip of a 200 µl pipette to make wounds. Then, each of the four 6-well dishes was replaced by a culture medium containing 1) angiogenin (1 µg/ml), 2) angiogenin (2 µg/ml), 3) angiogenin (5 µg/ml), and 4) angiogenin (10 µg/ml). At every 0 hour, 12 hours, 24 hours, and 48 hours, the wounded areas were measured by using the Image J software.

Figure 9:
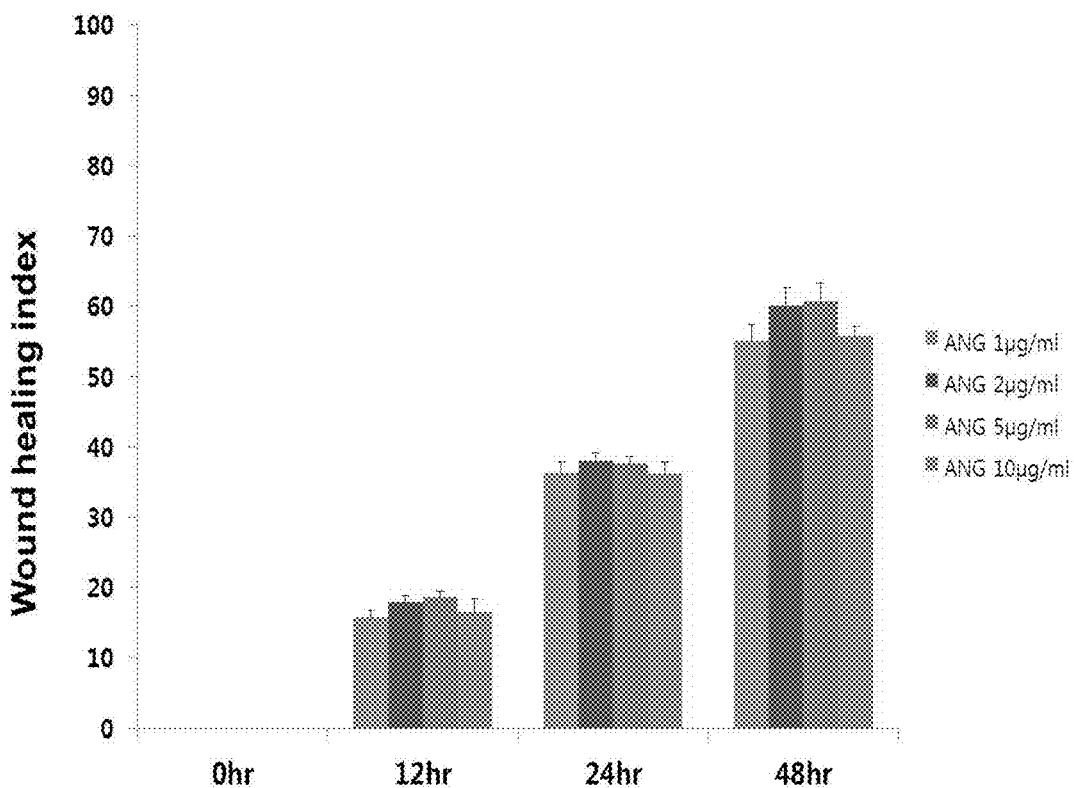
FIG. 9 is a graph showing wound healing index according to angiogenin treatment concentration and hours, the graph being obtained by culturing human corneal endothelial cells and treating the cells with angiogenin.

As a result, referring to FIG. 9, it was confirmed that the human corneal endothelial cells had the highest wound healing index in a group given 5 µg/ml angiogenin instillation, which was significantly higher than a group given 2 µg/ml angiogenin and a group given 5 µg/ml angiogenin instillation.

Example 3

Identification of Intracellular Pathway of Angiogenin

1. Analysis of In Vivo Wound Healing Aspects in a Group Given Both LY294002 and Angiogenin Instillations Experiments have been carried out to identify effects of angiogenin-induced PI3k-Akt signaling pathway in terms of recovering the corneal transparency after inducing damages to the corneal endothelium. After inducing freeze-damages to the corneal endothelium, 4 eyeballs out of 30 rabbit eyeballs in total were subjected to 50 µl of each of 200 µg/mL of angiogenin and 200 µM of PI3k-Akt pathway inhibitor, LY294002 instillation at a time every 3 minutes, and more particularly, 6 times a day for the first 2 days, and then, 4 times a day for the following one day. That is, the instillation was performed 16 times in total for 3 days. Then, 72 hours after inducing damages, i.e., at the time when the angiogenin instillation showed the highest effects as compared with the control group in the present research, the corneal transparency of the corneal endothelial cells was analyzed based on the slit-lamp microscopic examination method and the digital camera images taken in a diagonal direction, followed by being compared with a group given single instillation of angiogenin.

As a result, referring to FIG. 10A, the corneal transparency observed by the slit-lamp microscope at the observation time of 72 hours after inducing damages to the endothelium was not statistically significant. However, as shown in FIG. 10B, the group given both angiogenin and LY294002 instillations showed lower tendency (p=0.085) than the group given single instillation of angiogenin, and based on the obtained digital camera images and Table 2, the group given both angiogenin and LY294002 instillations was significantly different from the group given single instillation of angiogene for having 0% of fraction in terms of not including the corneal opacity and edema.

2. Analysis of In Vivo Wound Healing Aspects of Cultured Corneal Endothelial Cells in a Group Given Both LY294002 and Angiogenin Instillations Experiments have been carried out to identify whether angiogenin was involved its lower PI3k-Akt pathway in terms of healing the corneal endothelial cells. After causing in vitro wounds of the cultured human corneal endothelial cells, the cells were replaced by a culture medium containing a mixture of 5 µg/ml of angiogenin and 50 µM of LY294002. Afterwards, at every observation time of 6 and 24 hours, the wound healing index of the cells was calculated by using the Image J software, and compared with the wound healing index of the cells previously cultured using 5 µg/ml of angiogenin only.

Figure 11A:
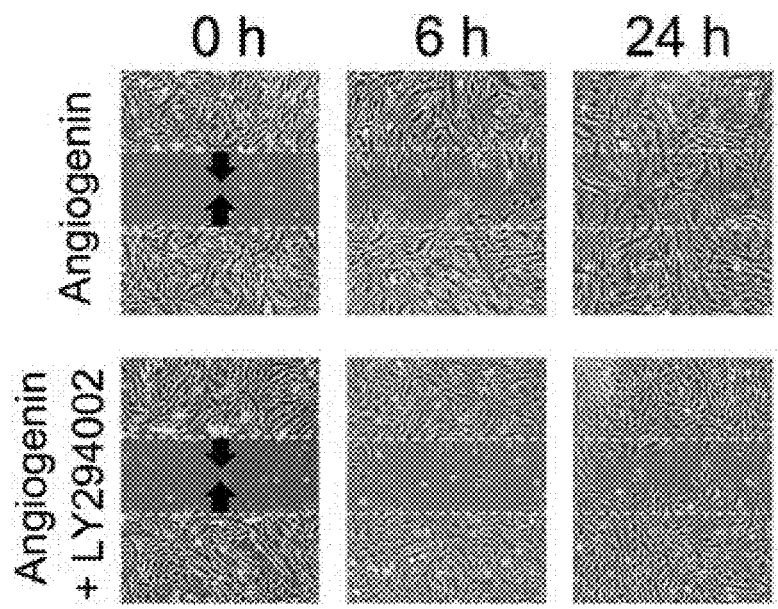
FIG. 11A shows optical microscope images taken at a magnification of 40× according to the hours and FIG. 11B is a graph showing wound healing index according to the hours.
Figure 11B:
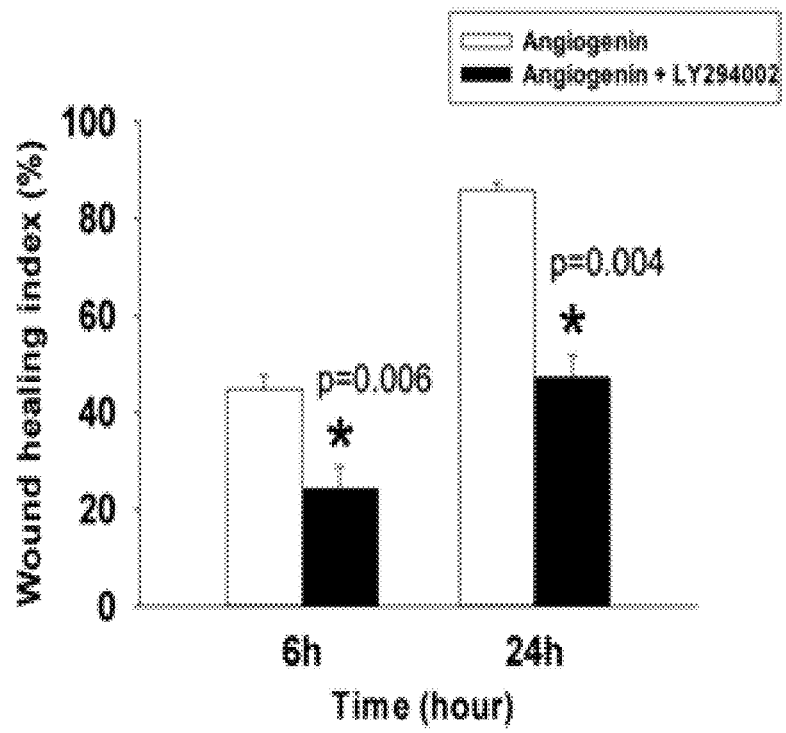

Referring to FIGS. 11A and 11B, the cultured human corneal endothelial cells exposed to the culture medium containing the mixture of angiogenin and LY294002 the has the wound healing indexes of 24.3±4.4% and 47.3±4.6% at every observation hours of 6 and 24 hours, respectively. These wound healing indexes were significantly lower than the wound healing indexes of 44.9±2.8% and 85.9±1.5% in the control group (p=0.006 and 0.004, respectively).

3. Western Blot Analysis of Expression Aspects of Protein Targeting Lower Pathway of Angiogenin The culture medium containing 5 µg/ml of angiogenin was treated with the cultured human corneal endothelial cells for 5 minutes, 10 minutes, 30 minutes, 1 hour, and 3 hours. Afterwards, according to the treatment times, expression aspects of Akt, eNOS, and Erk1/2 genes targeting the lower pathway of angiogenin were analyzed. First, a PRO-PREP™ protein extracting solution (Intron Biotechnology, Seongnam, Korea) was used to separate the total proteins from the corneal endothelial cells. The total proteins (30 µg/sample) were heat-treated at a temperature of about 100° C. for 5 minutes, and then, 10% sodiumdodecyl sulfate polyacrylamide (SDS-PAGE) gel was used to perform electrophoresis. The proteins separated according to molecular weights thereof were transferred to a polyvinylidene fluoride (PVDF) membrane, followed by being blocked by 5% BSA dissolved in 1× tris-buffered saline (TBS) at room temperature for 1 hour. Then, primary antibiotics (t-Akt, p-Akt, Erk, p-Erk, Cell Signaling Technology, Danvers, USA; eNOS, p-eNOS, Enzo Life Sciences, New York, USA; β-actin, Sigma Chemicals, St. Louise, USA) of t-Akt, p-Akt, t-Erk1/2, p-Erk1/2, t-eNOS, p-eNOS, β-actin diluted at a ratio of 1:1,000 in TBS-T (0.1% Tween 20 in TBS buffer) were treated with the PVDF membrane at a temperature of 4° C. for 16 hours. The PVDF membrane was washed by stirring at room temperature using a TBS-T stirrer three times each for 15 minutes. Then, secondary antibiotics (Bethyl Laboratories, Montgomerry, USA) linked to horseradish peroxidase (HRP) were diluted at a ratio of 1:2,000, so as to be stirred and incubated at room temperature for 1 hour. The PVDF membrane was washed by stirring again at room temperature using a TBS-T stirrer three times each for 15 minutes. The ECL western blotting detection reagent (Amersham Bioscience, Piscataway, USA) was used in terms of luminescence, and then, images were detected by using the same reagent for ChemiDoc™ XRS system (Bio-Rad, Hercules, USA).

Figure 12A:
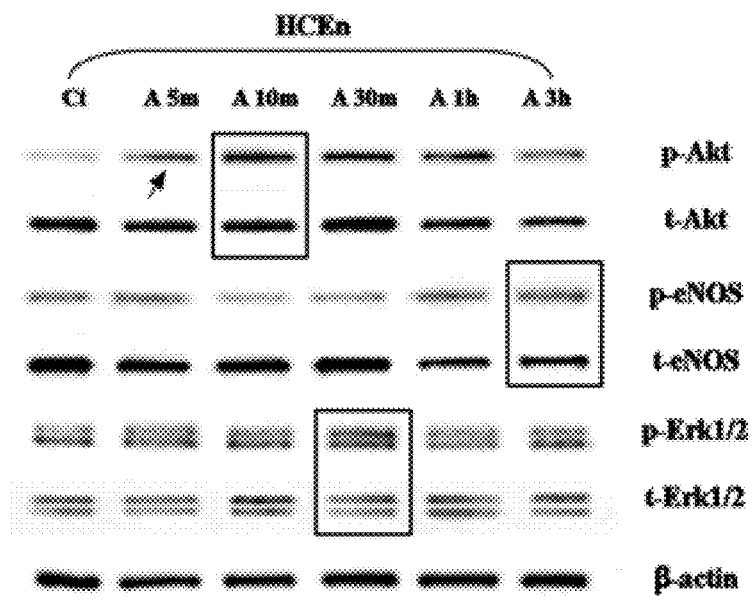
FIG. 12A is shows a result of western blot and FIG. 12B illustrates intracellular signal transduction system at a latter half of the angiogenin pathway, analyzed by the result of western blot.

As a result of the western blot, referring to FIG. 12A, the cultured human corneal endothelial cells treated with angiogenin had increased extent of relative expression of phosphate (p-form/t-form) as compared with the control group with respect to expression levels of all the Akt, eNOS, and Erk1/2 genes. The Akt was barely expressed in the control group, but after administrating angiogenin, the Akt showed the most clear increase in the expression.

Figure 12B:
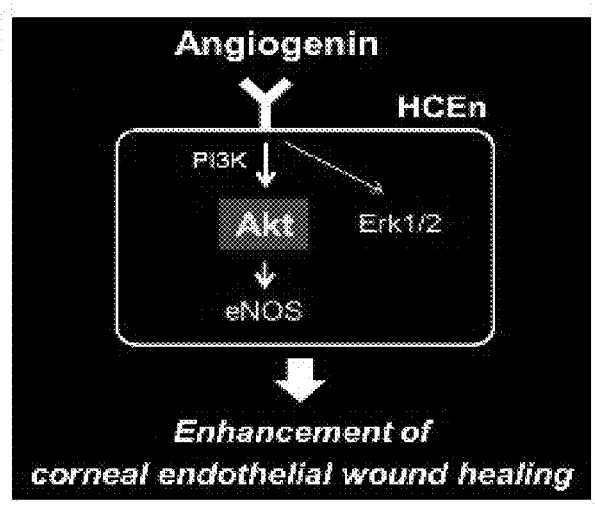

All the target proteins showed different aspects of the expression according the times. The p-Akt was maximally expressed after 10 minutes of angiogenin treatment, the p-Erk1/2 was maximally expressed after 30 minutes of angiogenin treatment, and the p-eNOS was maximally expressed after 3 hours of angiogenin treatment. Referring to FIG. 12B, the lower pathway of angiogenin's intracellular signaling system was confirmed to enhance the corneal endothelium wound healing.

TABLE 1

Grading criteria of corneal transparency in slit-lamp examination

| Grade | Characteristics |
|---|---|
| 0 | Completely transparent cornea |
| +0.5 | Vaguely cloudy, able to confirm only by lateral illumination |
| +1.0 | Extremely less turbid, difficult to confirm by diffuse lightening |
| +2.0 | Slightly turbid, able to confirm by slit lightening focus |
| +3.0 | Turbid in intermediate density, iris is partially covered |
| +4.0 | Turbid in high density, iris is completely covered |

(*statistically significant value)

TABLE 2

Corneal transparency during healing period of corneal endothelial wounds

| Time | 48 h | 72 h | 144 h | 192 h |
|---|---|---|---|---|
| Grade of corneal transparency (by using slit-lamp biomicroscope) | | | | |
| Control group | 4.00 ± 0 | 3.71 ± 0.18 | 2.00 ± 0.32 | 1.70 ± 0.44 |
| Y-27632 group | 4.00 ± 0 | 3.00 ± 0.41 | 1.38 ± 0.38 | 1.38 ± 0.38 |
| p value (vs. control group) | — | 0.114 | 0.225 | 0.606 |
| Angiogenin group | 4.00 ± 0 | 2.65 ± 0.37 | 1.29 ± 0.26 | 1.29 ± 0.26 |
| p value (vs. control group) | — | 0.042* | 0.096 | 0.442 |
| Angiogenin + LY294002 group | — | 3.75 ± 0.25 | — | — |
| p value (vs. angiogenin group) | — | 0.085 | — | — |
| Ratio of number of cornea without opacity and edema (digital camera images) | | | | |
| Control group | 0% | 0% | 0% | 16.7% |
| Y-27632 group | 0% | 14.3% | 14.3% | 14.3% |
| Angiogenin group | 10% | 20% | 37.5% | 50% |
| Angiogenin + LY294002 group | — | 0% | — | — |

(*statistically significant value)

TABLE 3

Central corneal thickness during healing period of corneal endothelial wounds
Central corneal thickness

| Time | 0 h | 48 h | 72 h | 144 h | 192 h |
|---|---|---|---|---|---|
| Control group | 350.2 ± 4.8 | >1,000 | >1,000 | 586.0 ± 22.3 | 443.5 ± 15.7 |
| Y-27632 group | 361.7 ± 3.4 | >1,000 | >1,000 | 571.6 ± 43.0 | 432.5 ± 332.2 |
| p value (vs. control group) | 0.086 | — | — | 0.806 | 0.806 |
| Angiogenin group | 350.4 ± 6.2 | >1,000 | >1,000 | 503.0 ± 21.1 | 390.3 ± 10.5 |
| p value (vs. control group) | 0.808 | — | — | 0.028* | 0.028* |

(*statistically significant value)

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of treating one or more corneal endothelium wounds in a subject in need thereof, comprising:
    a) providing a pharmaceutical composition comprising a therapeutically effective amount of angiogenin as an active ingredient; and
    b) administering the composition of step (a) to the cornea of the subject, wherein the wound or wounds are treated.

2. The method of claim 1, wherein the angiogenin activates the P13K/Akt/eNOS pathway.

3. The method of claim 1, wherein the content of the angiogenin is about 0.01 parts to about 10 parts by weight based on 100 parts by weight of the pharmaceutical composition.

4. The method of claim 1, wherein a formulation of the pharmaceutical composition is selected from the group consisting of instillations, injections, gels, suspensions, emulsions, drops, and solutions.

5. The method of claim 1, wherein the pharmaceutical composition further comprises at least one additive selected from the group consisting of carriers, excipients, disintegrants, sweetening agents, coating agents, swelling agents, lubricants, flavouring agents, antioxidants, buffers, bacteristats, diluents, dispersants, surfactants, binders, and lubricants.

* * * * *